(12) United States Patent
Schiendzielorz

(10) Patent No.: US 10,532,155 B2
(45) Date of Patent: Jan. 14, 2020

(54) INJECTION DEVICES TRIGGERED BY MECHANICAL KEY

(71) Applicant: Sanofi, Paris (FR)

(72) Inventor: Eva Schiendzielorz, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 15/509,276

(22) PCT Filed: Sep. 11, 2015

(86) PCT No.: PCT/EP2015/070866
§ 371 (c)(1),
(2) Date: Mar. 7, 2017

(87) PCT Pub. No.: WO2016/041869
PCT Pub. Date: Mar. 24, 2016

(65) Prior Publication Data
US 2017/0258994 A1    Sep. 14, 2017

(30) Foreign Application Priority Data

Sep. 15, 2014    (EP) ..................................... 14306417

(51) Int. Cl.
*A61M 5/172* (2006.01)
*A61M 5/142* (2006.01)
(Continued)

(52) U.S. Cl.
CPC .......... *A61M 5/172* (2013.01); *A61M 5/1452* (2013.01); *A61M 5/14248* (2013.01);
(Continued)

(58) Field of Classification Search
CPC .......... A61M 5/14244; A61M 5/14248; A61M 5/1452; A61M 5/14252
See application file for complete search history.

(56) References Cited

U.S. PATENT DOCUMENTS 5,785,688 A    7/1998  Joshi et al.
8,414,532 B2 *  4/2013  Brandt ................ A61M 5/1413
                                                 604/131
(Continued)

FOREIGN PATENT DOCUMENTS

EP    2 022 518    2/2002
EP    2 168 616    3/2010
(Continued)

OTHER PUBLICATIONS

International Search Report and Written Opinion in International Application No. PCT/EP2015/070866, dated Nov. 23, 2015, 13 pages.
(Continued)

*Primary Examiner* — Nathan R Price
*Assistant Examiner* — Tasnim Mehjabin Ahmed
(74) *Attorney, Agent, or Firm* — Fish & Richardson P.C.

(57) ABSTRACT

An injection device (100) comprises: a needle insertion mechanism (111); a medicament delivery arrangement (123) configured to cause injection of a medicament into a patient; and a cavity (102) having an opening (103) for receiving a key device (104). The injection device is configured to respond to detecting the presence of the key device in the cavity by triggering operation of the injection device. The specification also provides a method of controlling an injection device (100) including a needle insertion mechanism (111); a medicament delivery arrangement (123) configured to cause injection of a medicament into a patient; and a cavity (102) having an opening (103) for receiving a key device (104), the method comprising: responding to detecting the presence of the key device in the cavity by triggering operation of the injection device.

24 Claims, 5 Drawing Sheets

(51) Int. Cl.
*A61M 5/145* (2006.01)
*A61M 5/158* (2006.01)
*A61M 5/20* (2006.01)
*A61M 5/50* (2006.01)

(52) U.S. Cl.
CPC ............. *A61M 5/158* (2013.01); *A61M 5/20* (2013.01); *A61M 5/5086* (2013.01); *A61M 2005/14252* (2013.01); *A61M 2005/1585* (2013.01); *A61M 2005/206* (2013.01); *A61M 2005/2073* (2013.01); *A61M 2205/18* (2013.01); *A61M 2205/276* (2013.01); *A61M 2205/3334* (2013.01); *A61M 2205/50* (2013.01); *A61M 2205/6009* (2013.01); *A61M 2205/6018* (2013.01); *A61M 2205/6036* (2013.01); *A61M 2205/6054* (2013.01); *A61M 2205/6063* (2013.01); *A61M 2205/6072* (2013.01); *A61M 2205/8206* (2013.01); *A61M 2205/8262* (2013.01)

(56) References Cited

U.S. PATENT DOCUMENTS

| 2008/0009787 | A1* | 1/2008 | Jacobsen | A61M 5/14244 |
| | | | | 604/65 |
| 2009/0028824 | A1* | 1/2009 | Chiang | A61M 5/14248 |
| | | | | 424/85.7 |
| 2013/0338592 | A1 | 12/2013 | Calasso | |
| 2017/0043133 | A1* | 2/2017 | Amano | A61M 25/0606 |

FOREIGN PATENT DOCUMENTS

| EP | 2 762 183 | 8/2014 |
| EP | 3193973 | 7/2017 |
| WO | WO 02/068015 | 9/2002 |
| WO | WO 2009/144726 | 12/2009 |
| WO | WO 2013/173092 | 11/2013 |
| WO | WO 2016/041870 | 3/2016 |

OTHER PUBLICATIONS

International Preliminary Report on Patentability in International Application No. PCT/EP2015/070866, dated Mar. 21, 2017, 10 pages.

* cited by examiner

INJECTION DEVICES TRIGGERED BY MECHANICAL KEY

CROSS-REFERENCE TO RELATED APPLICATIONS

This application is a U.S. national stage application under 35 USC § 371 of International Application No. PCT/EP2015/070866, filed on Sep. 11, 2015, which claims priority to European Patent Application No. 14306417.8 filed on Sep. 15, 2014, the entire contents of which are incorporated herein by reference.

TECHNICAL

This disclosure relates to injection devices, and in particular to the triggering of operation of injection devices.

BACKGROUND

Injection or infusion pumps of the type known as patch pumps for delivering injections of medicament are known in the art. Another type of injection pump that is gaining traction is the bolus injector device.

Some bolus injector devices are intended to be used with relatively large volumes of medicament, typically at least 1 ml and maybe a few ml. Injection of such large volumes of medicament can take some minutes or even hours. Such high capacity bolus injector devices can be called large volume devices (LVDs).

To use a patch pump or bolus injector device such as an LVD, it is first supported on a suitable injection site of a patient. Once positioned, injection is initiated by the patient or another person (a user).

Typically a number of steps are be performed by the user before medicament injection can begin. Whilst handling the device in the pre-injection phase of operation it is possible that the user will accidentally initiate the device to cause injection and then medicament delivery. This may occur either when the device is not installed on the patient at all or when the device is only partly installed and is not secured at the correct location on the user. Improper triggering of the injection device is at best inconvenient and at worst can present safety issues.

It is an aim of the disclosure to provide an injection device with a triggering configuration that is relatively impervious to accidentally initiating operation of the injection device.

SUMMARY

A first aspect of the disclosure provides an injection device (100) comprising:
  a needle insertion mechanism (111);
  a medicament delivery arrangement (123) configured to cause injection of a medicament into a patient; and
  a cavity (102) having an opening (103) for receiving a key device (104),
wherein the injection device is configured to respond to detecting the presence of the key device in the cavity by triggering operation of the injection device.

This can provide an injection device that is insusceptible or relatively insusceptible to accidental or inadvertent operation.

The injection device may be configured to respond to detecting the presence of the key device in the cavity by causing commencement of delivery of medicament into the patient.

The injection device may be configured to respond to detecting the presence of the key device in the cavity by causing powering of the needle insertion mechanism to insert a needle into the patient.

The device may comprise a sensing arrangement (130) for sensing the presence or absence of the key device in the cavity, wherein the injection device is configured to respond to the sensing arrangement sensing the presence of the key device in the cavity by triggering operation of the injection device.

The injection device may be configured to retain the key device in the cavity. This can improve usability in that a user can leave the key device present in the cavity during the injection.

The injection device may be configured to retain the key device in the cavity by friction. Alternatively, the injection device may include a catch mechanism to retain the key device in the cavity.

The key device may be generally cylindrical. This can allow the key device can be particularly simple to use, since orientation of the key device to insert it in the cavity can be very easy.

The key device may have a length that is about the same as a length of the cavity. This can help prevent the key device being removed after insertion into the cavity.

The key device may have a length that is slightly longer than a length of the cavity. This can help prevent the key device being removed after insertion into the cavity whilst allowing easy insertion into the cavity.

The key device may be provided with an identifier that is readable by a or the sensing arrangement. Here, the injection device may be configured to respond to the sensing arrangement sensing the presence of the key device in the cavity by triggering operation of the injection device only if the identifier read by the sensing arrangement meets a predetermined criterion. This can help to prevent incorrect medicament administration. Alternatively or in addition, the injection device may be configured to limit the dose size and/or or delivery rate of medicament delivered dependent on the identifier read from the sensing arrangement. This can allow the use of different key devices to help a user adhere to desired medicament administration regime.

The device may be a bolus injector that is configured to be attached to a user for the duration of delivery of medicament.

The disclosure also provides a device fitted with a container of medicament.

The disclosure also provides a method of controlling an injection device (100) including a needle insertion mechanism (111); a medicament delivery arrangement (123) configured to cause injection of a medicament into a patient; and a cavity (102) having an opening (103) for receiving a key device (104), the method comprising:
  responding to detecting the presence of the key device in the cavity by triggering operation of the injection device.

BRIEF DESCRIPTION OF THE DRAWINGS

Embodiments of the disclosure will now be described, by way of example only, which reference to the accompanying drawings in which.

DETAILED DESCRIPTION OF THE EMBODIMENTS

In brief, this specification describes a medicament injection device, for instance in the form of a bolus injector device, patch pump or infusion pump, with a novel and inventive triggering configuration. In particular, the medicament injection device is provided with a cavity that is configured to receive a corresponding key device. An arrangement provided within the injection device is configured to detect (e.g. sense) whether the key device has been inserted into the cavity, and to respond to a detection that the key device is present in the cavity by triggering operation of the pump. Triggering may involve causing a needle insertion mechanism to insert a needle (which may be a hollow needle or a trocar) into a subject, for instance a patient, for receiving an injection of medicament and/or causing medicament delivery to be commenced. By triggering operation of the pump in response to detecting the key device being present in the cavity, the possibility of accidental triggering by unintentional pressing of a button or similar is avoided. In the case of triggering powering of the needle insertion mechanism, this feature may improve the safety of the device, since it can reduce the possibility of the needle incorrectly being extended from the device. In the case of triggering medicament delivery, this feature may also reduce the chance that the device is not used to deliver medicaments to a user, thereby reducing wastage. Advantageously, the injection device and the key device are configured so that the key device is retained in the cavity after it has been inserted into the cavity. This can simplify operation by a user of the injection device, which may be important particularly considering the device is being used to inject the user and to deliver medicament to them. This feature also provides a simple visual indication as to whether an injection device has already been used. The key device is so named because it can cause unlocking and/or activation of the injection device.

Figure 1:
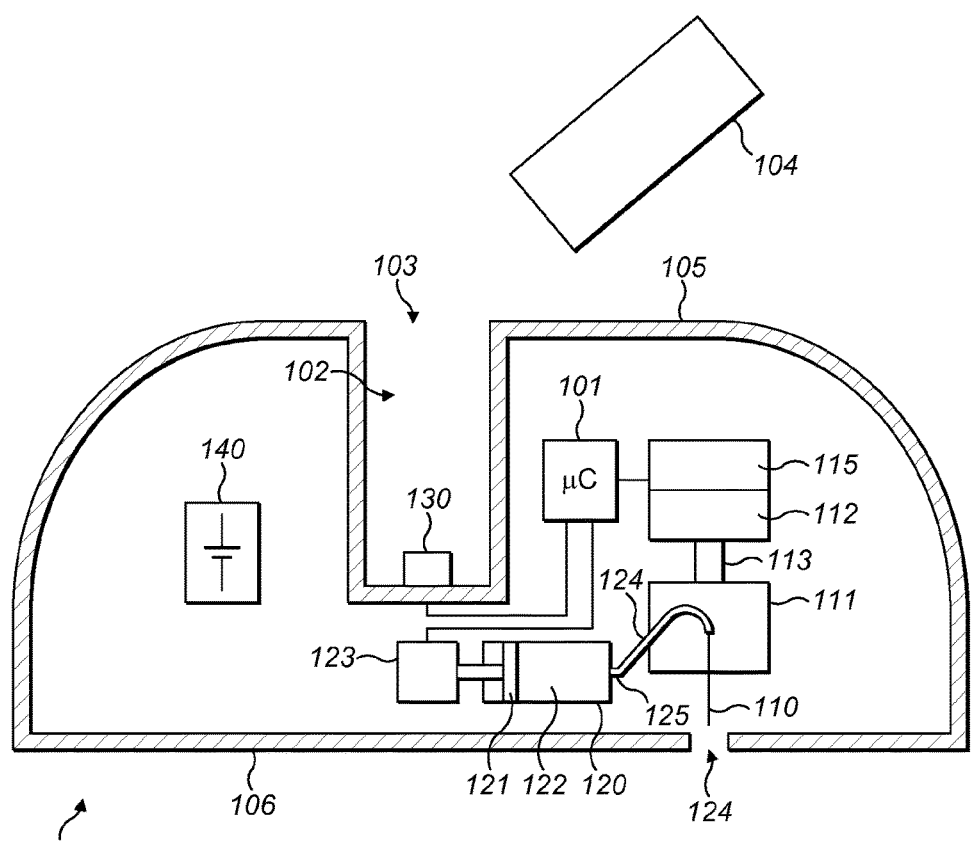
FIG. 1 is a schematic cross-section of a bolus injector device according to embodiments of the disclosure.

Referring firstly to FIG. 1, a bolus injector device according to various embodiments of the disclosure is shown in schematic form. The bolus injector device 100 includes numerous components, key ones of which will now be described. In the following, the user of the device is assumed to be the patient intended to receive medicament, although the user may be a different person to the patient.

The bolus injector device 100 includes a controller 101, that is configured to control operation of various components, as will be apparent from the below description.

The bolus injector device 100 includes a housing 105. The shape of the housing 105 may take any suitable form. Here, the housing 105 is shown to a have a cross-section that is substantially dome shaped. The housing 105 includes a lower surface 106, which is substantially planar and which is configured to be placed on the skin of a user during operation. The lower surface 106 may be provided with a layer of adhesive, so as to allow the bolus injector device 100 to be secured to the user's skin during medicament delivery. The housing 105 also includes an upper surface, which is curved in this example. The housing 105 defines an interior cavity in which most of the components of the bolus injector device 100 are located.

The housing 105 also defines a cavity 102 having an opening 103. The cavity 102 is generally cylindrical in shape and is longer than it is wide.

A key device 104 is configured so as be insertable through the opening 103 into the cavity 102. As shown, the key device 104 is cylindrical in shape. The width dimension of the key device 104 is selected so that the key device 104 can be inserted through the opening 103 into the cavity 102. The key device 104 is slightly longer than the length dimension of the cavity 102, for instance by between 2 and 10 mm. As such, when the key device 104 is fully inserted into the cavity 102 in the housing 105 of the patch device 100, the rear or uppermost end of the key device 104 protrudes slightly from the surface of the housing 105.

The bolus injector device 100 is provided with a sensor device 130. The sensor device 130 is configured to detect the presence of the key device 104 in the cavity 102. Particularly, the sensor device 130 is configured to detect whether the key device 104 is fully inserted into the cavity 102. This is achieved in this embodiment by locating the sensor device 130 at the bottom of the cavity 102.

The bolus injector device 100 includes a needle 110 and a needle insertion mechanism 111. The needle insertion mechanism 111 is controllable by the controller 101 to cause the needle 110 to extend through a needle aperture 114 in the housing 105 such as to pierce the skin of a patient. In FIG. 1, the needle 110 is shown in a retracted position, in which a tip of the needle 110 does not extend through the needle aperture 114. After the needle insertion mechanism 111 has operated, the needle 110 extends through the needle aperture 114. The tip of the needle 110 may for instance be inserted by distance of 5 to 10 mm through the needle aperture 114 so as to be inserted into tissue of a user to the same depth. The needle in this embodiment is a hollow needle having a bore.

The needle 110 is driven by the needle insertion mechanism 111 to be inserted into the user by a needle insertion mechanism drive 112. The needle insertion mechanism driver 112 may for instance be an electric motor or a spring release mechanism. Alternative forms are discussed below.

Energy for driving the needle insertion mechanism driver 112 comes from a needle driving energy source 115. The form of the needle driving energy source 115 corresponds to the form of the needle insertion mechanism driver 112, and is discussed below. A connecting mechanism 113 connects the needle insertion mechanism driver 112 to the needle insertion mechanism 111. The connecting mechanism 113 provides mechanical coupling between these two components.

The needle insertion mechanism driver 112 and the needle driving energy source 115 are controlled by the controller 101.

In some embodiments the needle insertion mechanism 111 is manually operated and is not powered from within the bolus injector device 100. In these embodiments, the needle energy driving source 115 and the needle insertion mechanism driver 112 are omitted. The needle insertion mechanism driver 112 is substituted with a mechanism for communicating user-applied work to movement of the needle 110 via the needle insertion mechanism 111. The communicating mechanism may translate user-provided work in the form of a rotation movement or a slide movement or a depression movement into movement of the needle 110 to be inserted into the tissue of the patient.

A medicament cartridge 120 is provided in the housing 105 of the bolus injector device 100. The medicament cartridge 120 may for instance include a vial formed of glass. A plunger 121 is provided within the cartridge 120 at an opposite end to a medicament delivery aperture 125. Between the plunger 121 and the end of the medicament cartridge 120 that includes the medicament delivery aperture 125 is defined a volume that is filled with medicament 122.

A medicament expelling driver 123 is mechanically coupled to the plunger 121. The medicament expelling driver 123 is controllable by the controller 101 to move the plunger 121 along the medicament cartridge 120. When so controlled, the force provided by the plunger 121 on the medicament 122 causes it to be expelled through the medicament delivery aperture 125 and along a medicament delivery tube 124 to the needle 110, in particular, the end of the needle 110 that is opposite to the end that is inserted into the user. When so operated, the medicament 122 is caused to be expelled through the bore of the needle 110. The expelling of the medicament in this way can be described as pumping. The flow rate of medicament expulsion can be set to some extent by configuration of the bolus injector device 100, but it is dependent also on physical characteristics of the patient's tissue at the injection site.

An electrical power source in the form of a battery 140 is provided. The battery 140 provides electrical power to the controller 101. It may also provide electrical power the medicament expelling driver 123, if this is an electrically driven device. The battery 140 may also constitute the needle driving energy source 115, that is to say the needle driving energy source 115 and the battery 140 may be combined into a single component.

Figure 2A:
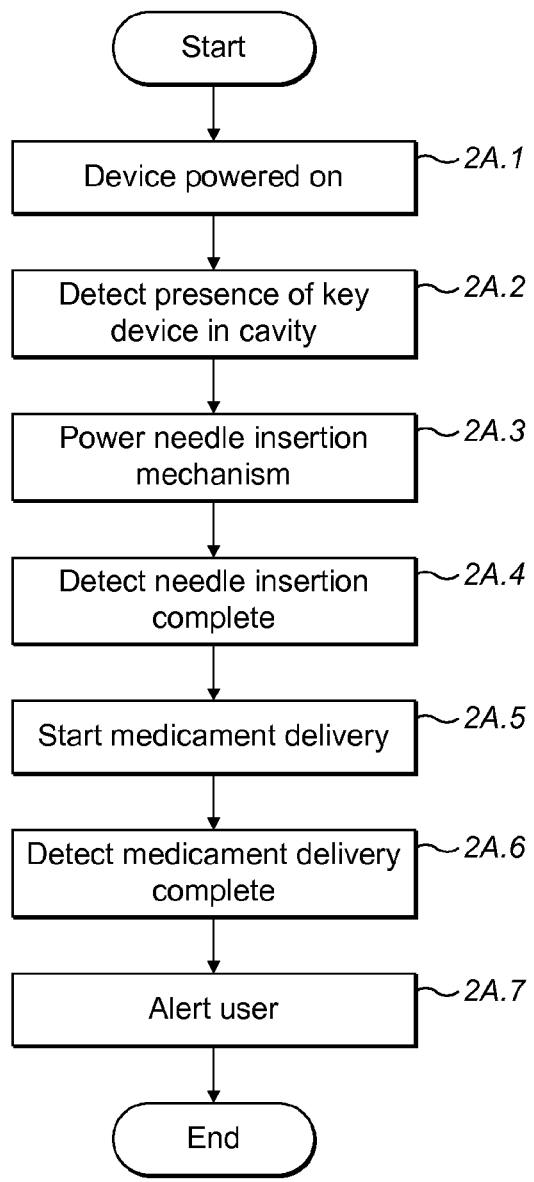
FIG. 2A is a flow chart illustrating operation of the FIG. 1 bolus injector device according to various embodiments of the disclosure.

A first type of operation of the bolus injector device of FIG. 1 will now be described with reference to FIG. 2A. Briefly, in the operation of FIG. 2A, the presence of the key device 104 in the cavity 102 triggers directly operation of the needle insertion mechanism 111. The operation of FIG. 2A starts and at step 2A.1 the device 100 is powered on. This may occur in response to a user removing an electrically isolating barrier that separates terminals of the battery 140 from the controller 101. It might alternatively occur in response to the user operating an electrical switch or other such component that forms part of the bolus injector device 100.

Following step 2A.1, the bolus injector device 100 at step 2A.2 detects the presence of the key device 104 in the cavity 102. The detection step 2A.2 occurs only when a user has inserted the key device 104 into the cavity 102 to the extent that sensing arrangement 130 is operated by the key device 104.

In response to detecting by the controller that the sensing arrangement 130 of the bolus injector device 100 has sensed the presence of the key device 104 in the cavity 102, at step 2A.3 the controller 101 powers the needle insertion mechanism 111. In particular, the controller 101 controls the needle driving energy source 115 and the needle insertion mechanism driver 112 to provide a driving force to the needle insertion mechanism 111 such that the needle 110 begins insertion into the user's tissue through the needle aperture 114.

This continues until at step 2A.4 the bolus injector device 100, in particular the controller 101, detects that the needle insertion is complete. This may occur for instance using feedback from the needle insertion mechanism driver 112, or using feedback from the needle insertion mechanism 111 or through a separate sensor (not shown).

Following step 2A.4, medicament delivery is started at step 2A.5. The medicament delivery may commence immediately in response to the detecting that the needle insertion is complete or it may require another trigger condition. For instance, it may be dependent on a user operating an electrical switch or some other input device on the bolus injector device 100. The trigger may alternatively be a timer expiring, where a timer is started when the needle insertion is detected to be complete at step 2A.4. For instance, the medicament delivery may start 5 or 10 seconds after the needle insertion is detected to be complete. The step 2A.5 of starting the medicament delivery comprises the controller 101 controlling the medicament expelling driver 123 to supply force on the plunger 121. This may expel the medicament 122 from the medicament cartridge 120 through the medicament delivery aperture 125 and along the medicaments delivery tube 124, and through the bore of the needle 110 into the tissue of the user.

At step 2A.6, the controller 101 of the bolus injector device 100 detects that the medicament delivery is complete. This may occur in any the suitable way. For instance, it may involve detection based on feedback provided by the medicament expelling driver 123 that the medicament expelling driver has stopped, for instance because it has reached the full extent of travel of the plunger 121. It may alternatively be detected in any other way, for instance in response to detecting that an integral of flow rate signals provided by a flow meter (not shown) exceeds a threshold, indicating that a desired medicament dose has been delivered through the needle 110.

In response to the bolus injector device detecting at step 2A.6 that the medicament delivery is complete, at step 2A.7 the bolus injector device alerts the user that the medicament delivery is complete. This can occur in any suitable way, for instance through controlling an illumination device such as an LED (not shown) to provide an alert signal such as a flashing alert or an alert of a certain colour.

After step 2A.7, the operation ends.

A second type of operation of the bolus injector device of FIG. 1 will now be described with reference to FIG. 2B. Briefly, in the operation of FIG. 2B the presence of the key device 104 in the cavity 102 triggers directly the start of delivery of the medicament. This operation is particularly suited to bolus injectors 100 that include a manually operable needle insertion mechanism 111.

Figure 2B:
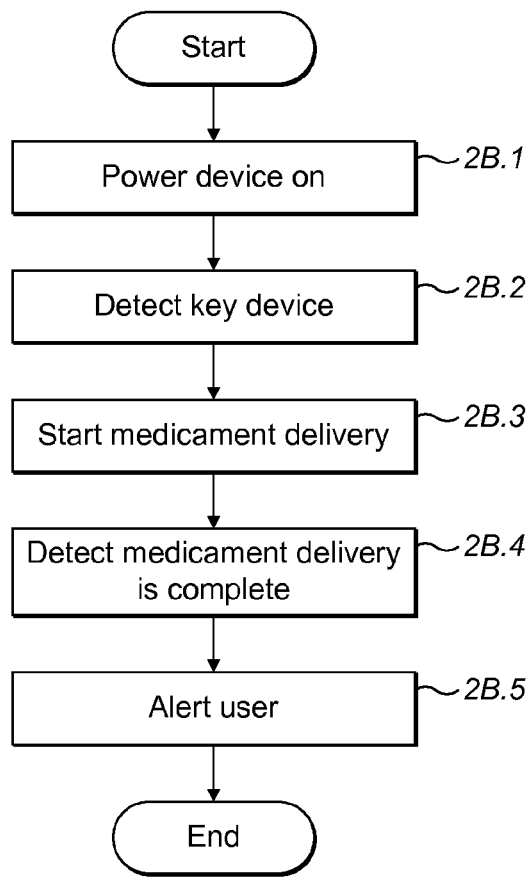
FIG. 2B is another flow chart illustrating operation of the FIG. 1 bolus injector device according to various embodiments of the disclosure.

The operation of FIG. 2B starts and at step 2B.1 the device 100 is powered on. This may occur in response to a user removing an electrically isolating barrier that separates terminals of the battery 140 from the controller 101. It might alternatively occur in response to the user operating an electrical switch or other such component that forms part of the bolus injector device 100.

Following step 2B.1, the bolus injector device 100 detects the presence of the key device 104 in the cavity 102. The detection step 2B.2 occurs only when a user has inserted the key device 104 into the cavity 102 to the extent that sensing arrangement 130 is operated by the key device 104.

In response to detecting by the controller that the sensing arrangement 130 of the bolus injector device 100 has sensed the presence of the key device 104 in the cavity 102, at step 2B.3 the controller 101 causes medicament delivery to be started.

Step 2B.3 may be a dual condition step in that the commencement of medicament delivery may be dependent both on the key device 104 being detected to be present in the cavity 102 and detecting that the (manually operated) needle insertion mechanism 111 has been operated to extend the needle into the patient. Detection that the needle insertion mechanism 111 has been operated may occur for instance using feedback from the needle insertion mechanism 111 or through a separate sensor (not shown).

The step 2B.3 of starting the medicament delivery comprises the controller 101 controlling the medicament expelling driver 123 to supply force on the plunger 121, which then causes expulsion of the medicament 122 from the medicament cartridge 120 through the medicament delivery aperture 125 and along the medicaments delivery tube 124 and through the bore of the needle 110 into the tissue of the user. Step 2B.3 may also involve providing an audible and/or visual alert so that the user is aware that medicament injection is commencing.

At step 2B.4, the controller 101 of the bolus injector device 100 detects that the medicament delivery is complete. This may occur in any the suitable way. For instance, it may involve detection based on feedback provided by the medicament expelling driver 123 that the medicament expelling driver has stopped, for instance because it has reached the full extent of travel of the plunger 121. It may alternatively be detected in any other way, for instance in response to detecting that an integral of flow rate signals provided by a flow meter (not shown) exceeds a threshold, indicating that a desired medicament dose has been delivered through the needle 110.

In response to the bolus injector device detecting at step 2B.4 that the medicament delivery is complete, at step 2B.5 the bolus injector device alerts the user that the medicament delivery is complete. This can occur in any suitable way, for instance through controlling an illumination device such as an LED (not shown) to provide an alert signal such as a flashing alert or an alert of a certain colour.

After step 2B.5, the operation ends.

Figure 3A:
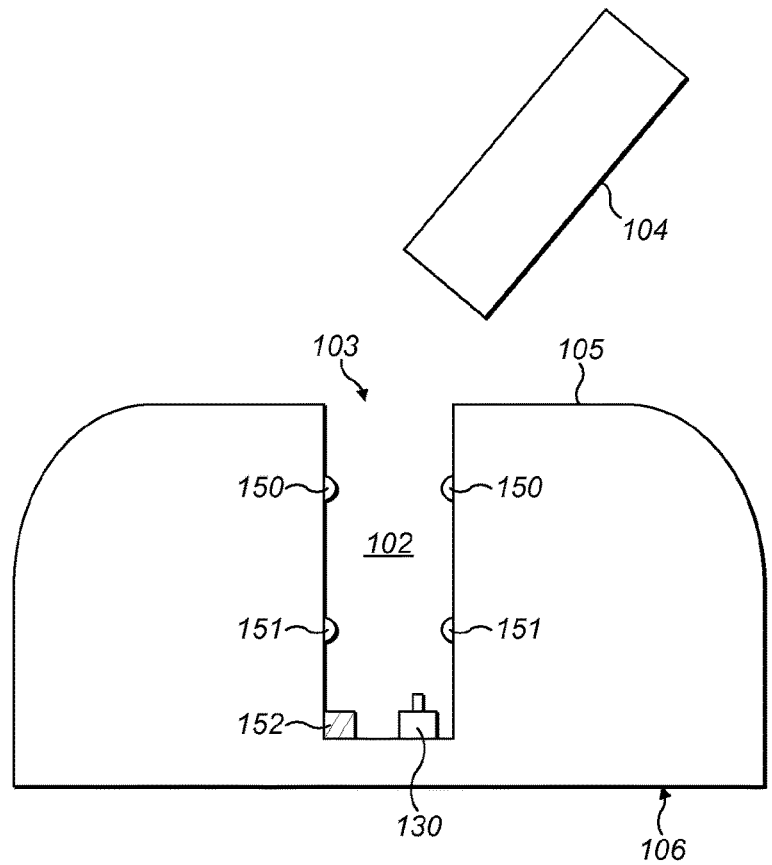
FIG. 3A is a schematic cross-section illustrating certain components of the FIG. 1 bolus injector device according to various embodiments of the disclosure.
Figure 3B:
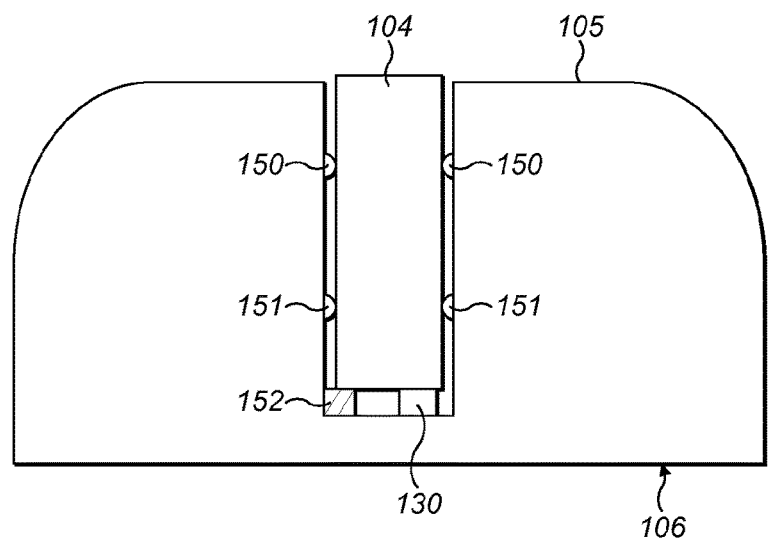
FIG. 3B illustrates the FIG. 3A bolus injector device with a key device inserted into a cavity thereof.

Referring now to FIG. 3A, one embodiment of the bolus injector device 100, in particular with details of the cavity 102, will now be described. FIG. 3A shows the bolus injector device 100 with the key device 104 external to the cavity 102 and FIG. 3B shows the bolus injector device with the key device 104 present in the cavity.

The FIG. 3 embodiment includes an arrangement for retaining the key device 104 in the cavity 102 once the key device 104 has been inserted into the cavity 102. In this embodiment, the bolus injector device 100 includes an arrangement including at least one resilient component that acts to maintain the key device 104 within the housing 105 by friction. In the FIG. 3 embodiment, one resilient component is a first ring 150. The ring 150 is secured to the innermost surface of the cavity 102. The ring 150 has an internal diameter that is approximately the same size as, or is slightly smaller than, the external diameter of the key device 104. The ring 150 is made of a resilient material, for instance a rubberised plastic. As such, the material of the ring 150 is deformable.

A second ring 150 has substantially the same form of the first ring 150. The first and second rings 150, 151 are separated from each other along the length of the cavity 102.

The opening 103 of the cavity 102 has a diameter that is larger than the diameter of the key device 104. As such, the key device 104 can easily be introduced by a user into the opening 103 and start its journey to the bottom of the cavity 102. When the lowermost end of the key device 104 reaches the first ring 150, the first ring 150 guides the end of the key device 104 to take a central position in the cavity, with respect to the longitudinal access of the cavity 102. At this time, the material of the ring 150 becomes compressed, and this results in frictional force being applied to the part of the external surface of the key device 104 that contacts the first ring 150. The ring 150 is maintained in its place within the cavity 102 by virtue of it being secured to the inner wall of the part of the housing 105 that defines the cavity 102.

As the key device 104 is inserted further down into the cavity 102, it contacts the second ring 150. The second ring 151 serves further to guide the key device 104 centrally within the cavity 102. It also compresses such as to provide a further frictional force against the external surface of the key device 104. Upon further movement of the key device 104, it eventually reaches the bottom of the cavity 102, as is shown in FIG. 3B. Here, the lowermost end of the key device 104 is made to rest against a step 152, which prevents further downward movement of the key device 104. At this position, the key device 104 has actuated the sensing arrangement 130, which in this embodiment is an electrical switch. Activation of the electrical switch 130 is achieved by the physical movement of one component of the switch, which is visible uppermost in FIG. 3A, to a position where it is retracted within a body of the switch 130 by the presence of the key device 104.

When the key device 104 is fully inserted into the cavity 102, as shown in FIG. 3B, it is retained in place by the frictional force provided by the first and second rings 150, 151 against the external surface of the key device 104.

The experience of the user when using the FIG. 3 embodiment is as follows. The user firstly locates the bolus injector device 100 on the desired injection site, and secures the bolus injector device to their skin at this site. This may be achieved by the provision of an adhesive layer on the surface 106. Next, the user grasps the key device 104, for instance between their thumb and forefinger. The user then manipulates the key device 104 so as to insert one end (in this embodiment it does not matter which end) into the opening 103. The user then aligns the key device 104 such that its longitudinal axis is approximately aligned with the longitudinal axis of the cavity 102 and pushes the key device 104 into the cavity 102. The user experiences some resistance to movement of the key device 104 once the end of the key device 104 reaches the first ring 150. This provides feedback to the user that the key device 104 is inserted correctly into the cavity 102. The user then continues to push the key device 104 down into the cavity 102. Once the key device 104 is sufficiently located within the cavity 102, they may switch from holding the key device 104 between their thumb and forefinger and instead push the key device 104 from the uppermost end (the end that is opposite the end that was inserted into the cavity 102). Because of the action of the first ring 150, the key device 104 is guided in the correct direction towards the bottom of the cavity 102.

Upon further pushing, the end of the key device 104, contacts the second ring 151. At this stage, the direction of movement of the key device 104 is further constrained, which provides further feedback to the user that the key device 104 is being inserted correctly. The second ring 151 also provides further resistance, indicating to the user that the key device 104 is approaching the bottom of the cavity 102.

After a little further movement, the bottom of the key device 104 contacts the step 152 and this is observable by the user because the force against movement of the key device 104 changes from the friction force provided by the first and second ring 150, 151 to the force needed to move the whole of the key device 104 and a bolus injector device 100 along with the tissue of the user upon which the bolus injector device 100 is installed. The user may also feel that the key device 104 has reached the bottom of the cavity 102 and contacted step 152 and the switch 130 by noticing a sensation at the tissue in which the bolus injector device 100 is installed.

Once the end of the key device 104 reaches the bottom of the cavity and activates the switch 130, the controller 101 causes triggering powering the needle insertion driving mechanism 112 to cause of the needle insertion mechanism 111 to extend the needle 110 (in the FIG. 2A embodiments) or the start of medicament delivery (in the FIG. 2B embodiments).

Once the key device 104 has been fully inserted into the cavity 102, the uppermost end of the key device 104 may be substantially flush with the uppermost surface of the housing 105, or it may stand slightly proud of the upper surface of the housing 105. Selecting the length of the key device 104 to be slightly longer than the height of the cavity minus the height of the step 152 (by between 2 and 7 or between 2 and 10 mm for instance) makes it easier for the user to insert the key device 104 into the cavity 102, particularly if the key device 104 has a relatively small width dimension and the user wishes to push the key device 104 for the final part of its travel to the bottom of the cavity 102 using their thumb. However, the length of the key device 104 is selected so that when it is fully inserted a user cannot grasp the free end with their thumb and forefinger. This helps to prevent the user attempting to remove the key device.

An alternative embodiment will now be described with reference to FIG. 4. With this Figure, reference numerals are reused from the earlier Figures for like elements.

Figure 4:
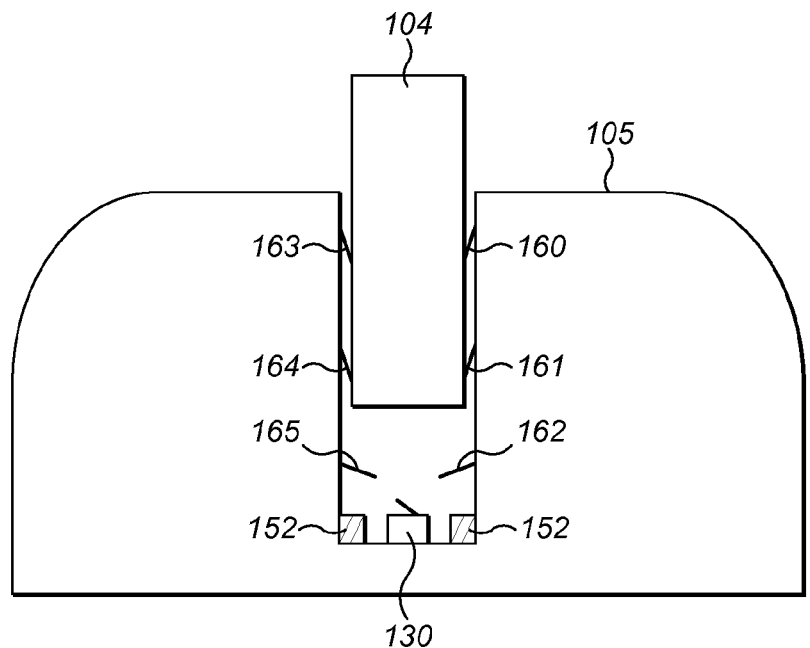
FIG. 4 is a schematic cross-section through a bolus injector device according to other embodiments of the disclosure.

In the FIG. 4 embodiment, the rings 150, 151 from FIG. 3 are omitted. Instead, plural fingers, six of which are shown at 160-165, are provided on the innermost surface of the cavity 102.

The fingers are secured at one end to the innermost surface of the cavity 102 and extend towards the centre of the cavity 102. The fingers 160 to 165 either are formed of a resilient material or are resiliently connected to the wall of the cavity 102. The fingers 160 to 165 are directed at least slightly in a downward direction in the cavity 102. This is best seen from the fingers 162 and 165 in FIG. 4.

The lengths of the fingers 160 to 165 are selected such that their innermost ends are located a distance from the centre of the cavity that is less than the radius of the key device 104. As such, the key device 104 contacts the fingers 160-165 when it is inserted in to the cavity 102.

In FIG. 4, the key device 104 is shown partly inserted into the cavity. It can be seen from this Figure that, as the key device 104 contacts some of the fingers 160 to 165, the fingers are resiliently moved away from the longitudinal axis of the cavity 102. The fingers 160-165 thus provide guidance of the key device 104 as it moves along the cavity 102. Additionally, they provide a frictional resistance to movement of the key device 104 into the cavity 102. However, the downwards orientation of the fingers 160-165 means that the resistance to movement of the key device 104 in the opposite (upwards) direction is much greater. This serves to maintain the key device 104 within the cavity 102 whilst providing relatively little resistance to insertion of the key device 104 into the cavity 102.

When the key device 104 reaches the bottom of the cavity 102, it activates the switch 130 and thus causes triggering of the powering of the needle insertion mechanism 111 to insert the needle 110 into the user. When located at a position fully inserted into the cavity 102, the key device 104 is maintained in place by operation of the fingers 160-165.

FIG. 4 shows an alternative form for the step 152. Here, the step is annular in form, so supports the key device 104 around the entire circumference of the lower end of the key device 104. It may alternatively have the form of a broken annulus.

A further embodiment will now be described with reference to FIG. 5. Reference numerals are retained from earlier embodiments for like elements.

Figure 5:
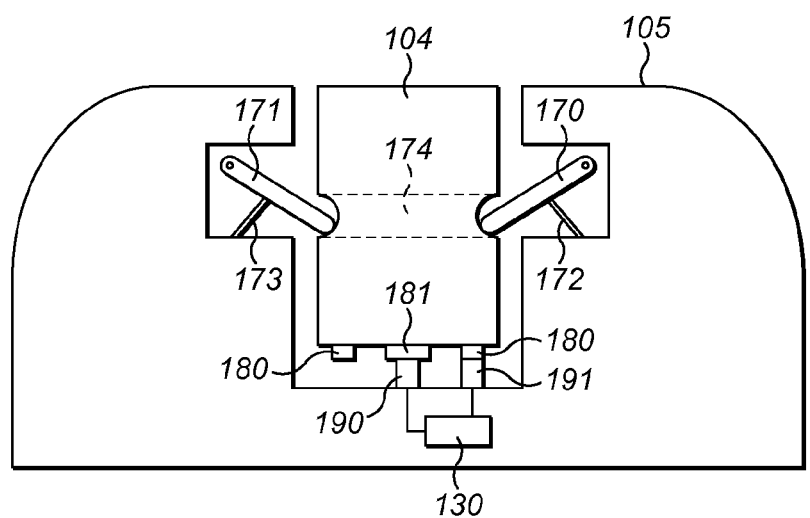
FIG. 5 is a schematic cross-section of a bolus injector device according to further embodiments of the disclosure.

The FIG. 5 embodiment deviates from the earlier embodiments in two different ways. The first relates to a way in which the key device 104 is retained within the cavity 102 once it has been inserted. The second is in the nature of the key device 104 and the nature of the sensing arrangement 130. It will be appreciated that these elements are separable from one another, and that this constitutes an explicit disclosure of an embodiment with the sensing arrangement of FIG. 5 separate from the key retaining configuration, and constitutes another embodiment including the key device retaining mechanism of FIG. 5 and a different sensing arrangement, for instance the sensing arrangement of the FIG. 3 or FIG. 4 embodiments.

In the FIG. 5 embodiment, the key device 104 includes a feature on its external surface that serves to assist in retaining the key device 104 within the cavity 102. In particular, the key device 104 includes a recess of the side thereof. In the FIG. 5 embodiment, the recess takes the form of a channel or groove 174 that extends all the way around the circumference of the key device 104.

The channel 174 interacts with arms 170, 171 of the bolus injector device 100 when the end of the key device 104 is located at the bottom of the cavity 102. In particular, the first arm 170 is pivoted at the end that is rightmost in the drawing and is sprung in a downwards direction as shown such as to maintain the orientation as shown in FIG. 5. A counter spring component or biassing element 172 is configured so as to force the first arm 170 in the opposite direction. Thus, in the absence of external forces, the first arm 170 and the biassing element 172 provide forces against each other and maintain a certain positional relationship for the first arm 170.

A corresponding arrangement is formed on the opposite side of the key device 104 and comprises a second arm 171 and a second biasing element 173.

The downward orientation of the first and second arms 170, 171 allows the arms to be pushed away, against the forces provided by the biasing elements 172 and 173, when the lowermost end of the key device 104 contacts the first and second arms 170, 171 as the key device 104 is introduced through the opening 103 into the cavity 102. The first and second arms 170, 171 remain forced downwards and slightly outwards as the key device 104 is moved downwards into the cavity. As the location of the groove 174 becomes aligned with the ends of the first and second arms 170, 171, the arms are allowed to spring slightly inwards and upwards, so as to enter the groove 174. Thereafter, movement of the key device 104 in an upwards direction, as shown in FIG. 5, is prevented by the first and second arm 170, 171. Movement is prevented because the arms 170, 171 are oriented in a downwards and inwards direction and in substantially the opposite direction to a force that is provided on the arms by action of the profile of the groove 174 as the key device 104 is forced in an upwards direction. Thus, removal of the key device 104 is prevented. The first and second arms 170, 171 and the groove 174 thereby form a catch arrangement which allows the key device 104 to be moved in one direction but then prevent it being moved in the opposite direction. Other forms of catch arrangement that achieve the same or similar affect will be apparent to the person skilled in the art.

The key device 104 in this embodiment is a battery, in that it includes electrical cells and is operable to provide electrical energy. The battery 104 includes at least positive and negative terminals which are shown as 180 and 181 in FIG. 5. In this embodiment, one terminal 181 is formed centrally with respect of the axis of the battery 104 and the second terminal 180 is provided radially. The second terminal 180 has the form of the ring in this embodiment. This allows the battery 104 to be inserted into the cavity 102 in any rotational orientation.

Located at the bottom of the cavity and coupled mechanically to the housing 105 are first and second electrical terminals 190, 191. The first and second electrical terminals 190, 191 are located so as to contact the terminals 180, 181 of the battery 104 when the battery 104 is located within the cavity 102. The terminals 190, 191 of the bolus injector device 100 may take any suitable form, and may for instance be metallic protrusions. The terminals 190, 191 may be resilient, for instance by being in the form of a spring, so as to maintain a reactive force against the terminals 180, 181 of the battery 104.

In the FIG. 5 embodiment, the sensing arrangement 130 comprises a detector that is configured to detect the presence of an electrical voltage across the terminals 190, 191. Such a voltage indicates the presence of a battery 104 within the cavity 102 and connected to the terminals 190, 191.

As with the other embodiments, the patch device 100, in particular, the controller 120, is configured to detect the presence of the key device in the cavity (in this instance by detecting a voltage across the terminals 190,191) and to respond to the detection by triggering powering the needle insertion driving mechanism 112 to cause the needle insertion mechanism 111 to insert the needle 110 into the user (in the FIG. 2A embodiments) or the start of medicament delivery (in the FIG. 2B embodiments).

Although in FIG. 5 the terminals 180, 181 of the battery as shown as protruding from the lowermost surface of the battery 104, they may instead be recessed. Recessing the terminals 180,181 of the battery 104 reduces the possibility of shorting of the battery, which could otherwise occur whilst the battery is not inserted into the cavity 102.

In embodiments in which the key device 104 doubles as a battery, the battery 140 may be omitted. Also, if the needle insertion mechanism drive 112 is an electrically operated driver, then the needle driving energy source 115 can be omitted and the electrical power needed for driving the needle insertion mechanism driver 112 can come instead from the key device 104.

The dual function of the battery and key device 104 in the FIG. 5 embodiment provides a number of advantages. Primarily, it avoids the need for a separate arrangement for isolating the battery from the electrical components of the bolus injector device 100 prior to operation. Thus, for instance, it avoids the need for the user to perform a separate step of inserting the battery (additional to initiating injection or commencing medicament delivery) or of connecting the battery to the component. Reducing the number of steps needed to be performed by the user in operating an injection device is generally considered as desirable.

In some embodiments, the key device 104 is provided with identifying information and the sensing arrangement 130, or a separate sensing arrangement (not shown) is configured to read the identifying information from the key device 104. In these embodiments, the controller 101 is configured to trigger operation of the needle insertion mechanism 111 (in the FIG. 2A embodiments) or the start of medicament delivery (in the FIG. 2B embodiments) only on detecting that the identifier read from the key device 104 by the sensing arrangement 130 meets a predetermined criterion.

In some embodiments, the controller 101 is configured to cause operation of the needle insertion mechanism 111 and/or the starting of medicament delivery only on detecting that the identifier read from the key device 104 by the sensing arrangement 130 is the same as or otherwise be validated by data (for instance by satisfying a test including deriving the hash of the identifier) stored in a memory (not shown) of the bolus injector device 100. By requiring the identifier to be validated by the bolus injector device 100, patients can be protected from counterfeit medicament cartridges. Additionally, this can provide protection against substance misuse.

In these embodiments and in other embodiments, the controller is configured to cause dispensing of a quantity of medicament that is dependent on the identifier read from the key device 104 and then to cease dispensing. In these embodiments, the patient may be provided with a number of different keys that together represent a medicament administration regime. By using the keys in the correct order, the patient can be medicated according to the regime without needing manually to set a required dose or select an appropriate medicament cartridge or such like. Some medicaments are intended to be used initially with a relatively low bolus dose and then the bolus dose is increased over time, and adherence to such regimes is simplified by the bolus injector device 100 being configured in this way.

In other embodiments, the controller is configured to cause dispensing of medicament at a dispensing rate (in terms of dose per unit time, but which may not be a constant rate) that is dependent on the identifier read from the key device 104. In these embodiments, the patient may be provided with a number of different keys that together represent a medicament administration regime. By using the keys in the correct order, the patient can be medicated according to the regime without needing manually to set a required dose or select an appropriate medicament cartridge or such like. Some medicaments are intended to be used initially with a relatively low basal delivery rate and then the basal delivery rate is increased over time, and adherence to such regimes is simplified by the bolus injector device 100 being configured in this way.

The identifier may be provided on the key device in any suitable form, for instance in visibly encoded form, for instance as a bar code, QR code, or other visual encoding means. It may alternatively be provided in an RFID transducer, or as a frequency of an oscillator or crystal included in the key device 104. Whatever the form for the identifier, the sensing arrangement 130 (or another sensing arrangement) takes a form such as to be able to read the identifier from the key device 104.

The injection device is configured to deliver the medicament subcutaneously, although it may instead be configured for intradermal injection, for instance using a microneedle, or for injection in some other manner.

The bolus injector device may be of the type known as a Large Volume Device (LVD). An LVD injection device is configured to dispense a relatively large dose of medicament, in particular at least 1 ml and typically up to 2.5 ml, but possibly up to 10 ml.

The bolus injector device is configured to deliver a bolus of the respective medicament to bring a volume of the medicament into a patient's body within a predetermined time. The injection rate, however, may not be critical, i.e. tight control may not be necessary. However, there may be an upper (physiological) limit to the delivery rate in order to avoid damage to the tissue surrounding the delivery site. The time taken to deliver a bolus dose of medicament may be between a few minutes and many hours depending on a number of factors including the quantity (volume) of medicament, the viscosity of the medicament and the nature of the injection site at which the injection device is intended to be used.

From a user or Health Care Professional perspective, it is desirable for an injection device to be configured to minimally impact the patient's lifestyle and schedule, providing the patient with minimal reminder of his or her disease between the injections. The treatment schedule for therapies is usually intermittent, i.e. may be one injection per week, one injection every other week, or one per month. Therefore, the patient usually has no routine in dealing with his or her disease, and hence has minimal routine/experience in performing the required injections. Thus, configuration of the injection device to simplify its operation by patients is highly desirable.

Because it is intended for bolus operation, the configuration of the injection device is quite different compared to an injection device that is intended to be used for basal operation. Also, its use is quite different. For instance, a basal type insulin pump generally is relatively expensive as it includes many sophisticated diabetes specific features like programmable delivery rate profiles, bolus calculators etc. Further, the connection to the body via an infusion set allows the patient to handle and manipulate the pump in his/her field of view while the therapy is ongoing. Further, diabetes patients usually have a routine in setting-up the infusion set, connecting and operating the pump, and disconnecting the pump temporarily for events like taking a shower so not to expose the pump to water. In contrast, the bolus injector devices described above can be relatively simple and inexpensive devices. They may be provided as single-use devices, which cannot be recharged with medicament, which further reduces complexity and cost.

The term "drug" or "medicament", as used herein, means a pharmaceutical formulation containing at least one pharmaceutically active compound. In some embodiments, the pharmaceutically active compound can have a molecular weight up to 1500 Da or may include a peptide, a protein, a polysaccharide, a vaccine, a DNA molecule, an RNA molecule, an enzyme, an antibody or a fragment thereof, a hormone or an oligonucleotide, or a mixture of the above-mentioned pharmaceutically active compound. Various types or subtypes of compounds are also contemplated. For example, RNA may include RNAi, siRNA, or miRNA. In other embodiments, the pharmaceutically active compound can be useful for the treatment or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis or rheumatoid arthritis. In some embodiments, the pharmaceutically active compound can comprise at least one peptide for the treatment or prophylaxis of diabetes mellitus or complications associated with diabetes mellitus such as diabetic retinopathy. The pharmaceutically active compound can also comprise at least one human insulin or a human insulin analogue or derivative, glucagon-like peptide (GLP-1) or an analogue or derivative thereof, or exendin-3 or exendin-4 or an analogue or derivative of exendin-3 or exendin-4 or a pharmaceutically acceptable salt or solvate thereof.

Insulin analogues can include, for example, Gly(A21), Arg(B31), Arg(B32) human insulin; Lys(B3), Glu(B29) human insulin; Lys(B28), Pro(B29) human insulin; Asp (B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives can include, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 can include, for example, Exendin-4(1-39).

Hormones can include, for example, hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, or Goserelin.

A polysaccharide can include, for example, a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies can include generally globular plasma proteins (~150 kDa) that are also known as immunoglobulins which share a basic structure. As they can have sugar chains added to amino acid residues, they may also be classified as glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that can include four polypeptide chains; two heavy chains and two light chains connected by disulfide bonds between cysteine residues. Each heavy chain can be about 440 amino acids long; each light chain can be about 220 amino acids long. Heavy and light chains may each contain intra-chain disulfide bonds which stabilize their folding. Each chain is composed of structural domains called Ig domains. These domains typically contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of antibodies can be similar, the unique property of a given antibody is determined by the variable (V) regions, as detailed above. More specifically, variable loops, often three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is usually the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their inter-chain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H inter-chain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion. Pharmaceutically acceptable solvates are for example hydrates.

In some embodiments, medicaments of various viscosities can be injected. For example, viscosity could range from about 3 to about 50 cP. In other embodiments, viscosity could be less than about 3 cP or greater than about 50 cP.

Injection can further include delivering a medicament to a sub-cutaneous, an intra-muscular, or a transdermal location within a patient's body. The medicament can be in the form of a liquid, gel, slurry, suspension, particle, powder, or other type.

Typical injection volumes can range from about 1 mL to about 10 mL. Rates of injection may be about 0.5 mL/min, about 0.2 mL/min, or about 0.1 mL/min. Such injection profiles may be generally constant in flow rate, generally continuous in duration, or both generally constant and generally continuous. These injections can also occur in a single step of administration. Such injection profiles may be referred to as bolus injections.

Delivery devices functioning with such medicaments may utilize a needle, cannula, or other injection element configured to deliver a medicament to the patient. Such an injection element may, for example, have an external size or diameter of 27 G or less. Further, the injection element could be rigid, flexible, and formed using a range of one or more materials. And in some embodiments, the injection element may include two or more components. For example, a rigid trocar may operate in conjunction with a flexible cannula. Initially, both the trocar and cannula may move together to pierce the skin. The trocar may then retract while the cannula remains at least partially within the target tissue. Later, the cannula may separately retract into the delivery device.

It will be appreciated that the above described embodiments are merely illustrative and not limiting on the disclosure, the scope which is defined only by the appended claims. Various alternatives will be apparent to the skilled person, and a number of such alternatives will now be described.

The key device 104 may take any suitable shape. Although in the above the key device 104 is longer than it is wide, it may instead be wider than it is long, or it may be spherical or take some other form. Although in the above the key device 104 is generally cylindrical, it may instead have some other shape. It may for instance have a square, rectangular or star-shaped cross section. Providing the key device 104 with a substantially constant cross section along its length makes it easier for a user to understand how the key device 104 should be used, although in some embodiments it does not have a constant cross section along its length.

In the FIGS. 3 and 4 embodiments, it is the shape of the key device 104 that results in operation of the sensing arrangement 130. As such, the other aspects of the configuration of the key device, 104, such as the material, colour, finish, etc. may not be critical to operation of the key device 104 in relation to the sensing arrangement 130. As such, the key device 104 in these embodiments may be made of any suitable material, such as for instance wood, plastic, ceramic, etc.

In other embodiments, the nature of the key device 104 other than its shape and size forms part of the key characteristics of the key device 104. Some such embodiments will now be described.

In one embodiment, the sensing arrangement 130 comprises an arrangement that is sensitive to magnetic fields. For instance, the sensing of arrangement of 130 may be a Reed switch or such like. Here, the key device 104 is formed of a magnetised material, for instance a ferrous material. In this embodiment, the correct presence of the key device 104 in the cavity 102 is detected by the sensing arrangement 130 detecting that a magnetic field resulting from the key device 104 being located fully within the cavity 102 is present. In this embodiment, triggering of the needle insertion mechanism 111 and/or medicament delivery cannot be achieved by something having dimensions that allows it to be located within the cavity 102 but which is not formed of the correct material and/or does not have the relevant magnetic properties.

In another embodiment, the sensing arrangement 130 is an optical sensing arrangement and detects the presence or absence of the sensing device 104 by detecting an optical condition. For instance, a light source may illuminate a photodetector and the light source and photodetector may be arranged such that a path between the two devices is blocked when the key device 104 is located fully within the cavity 102. In this way, the presence or absence of the key device 104 can be detected through examination of the signal provided by the photodetector.

There are various other possible forms for the sensing arrangement 130, as will be apparent to the skilled person.

In other embodiments, the key device 104 includes an element, for instance in the form of a ring, that can be gripped by a user. Here, the user can grasp the element and remove the key device 104 from the cavity if they wish to stop medicament delivery. In these embodiments, the controller 101 is configured to respond to detection that the key device 104 has been removed from the cavity 102 by causing the medicament expelling driver 123 to stop causing the delivery of medicament. This can be a particularly useful feature whether the medicament delivery is basal or bolus. The user may wish to stop medicament delivery so they can remove the bolus injector device 100 (for instance to take a swim) or for any other reason.

In some embodiments, the presence of the key device 104 in the cavity 102 is detected through a mechanical arrangement. For instance, a catch mechanism that prevents releasing energy stored in a spring to insert the needle, via the needle insertion mechanism 111, is caused to be released by the presence of the key device 104 at the correct location in the cavity 102. Alternatively, a catch mechanism that prevents releasing energy stored in a spring to expel the medicament through the needle 110 into the user is caused to be released by the presence of the key device 104 in the cavity 102. In either case, the key device 104 can release the catch by contacting the catch directly or by contacting it through an intermediary component or mechanism.

In some other embodiments, the presence of the key device 104 in the cavity 102 is detected through detecting that an electrical circuit is completed. In these embodiments, electrical contacts are provided at a position in the cavity 102 where they can be contacted by the key device 104 when inserted into the correct location. The key device 104 is electricaly conductive, or at least includes an electrically conductive part at the location that contacts the elecrrical contacts located in the cavity.

In the above, the injection device is a bolus injector device. The injection device may instead be a patch pump, another type of infusion pump, an autoinjector or some other form of injection device. The embodiments of the disclosure are particularly suited to bolus injections, but the injection device may instead be of the basal type.

The needle insertion mechanism driver 112 may take any suitable form. It may for instance include an electric motor and a gear mechanism that causes insertion of the needle 110 into the user. It may alternatively be a mechanical spring based mechanism. In this case the needle driving energy source 115 is a preloaded spring, and the needle insertion mechanism driver 112 is a spring release mechanism that causes force from the spring to be communicated to the needle insertion mechanism 111 thereby to insert the need 110 into the user.

Alternatively, the needle insertion mechanism driver 112 may be a gas or fluid pressure operated mechanism, in which case the needle driving energy source 115 is either a reservoir of pressurised gas or a chemical system in which two or more chemicals are mixed together to produce gas or fluid pressure.

The invention claimed is:

1. An injection device comprising:
   a needle insertion mechanism;
   a medicament delivery arrangement configured to cause injection of a medicament into a patient;
   a cavity comprising an opening configured to receive a key device such that a possibility of accidental triggering by unintentional pressing of a button or similar is avoided; and
   a sensing arrangement configured to sense a presence or an absence of the key device in the cavity,
   wherein the injection device is configured to respond to detecting that the key device, which has previously been external to the cavity, has been inserted into the cavity to be present in the cavity by powering of the needle insertion mechanism to insert a needle into the patient.

2. The device as claimed in claim 1, wherein the injection device is configured to respond to detecting that the key device has been inserted into the cavity to be present in the cavity by causing commencement of delivery of medicament into the patient.

3. An injection device as claimed in claim 2, wherein the injection device further comprises a controller, wherein the controller is configured to respond to detecting that the key device has been inserted into the cavity by sequentially: causing powering of the needle insertion mechanism to insert the needle into the patient; and commencing delivery of the medicament into the patient.

4. The injection device as claimed in claim 1, wherein the injection device is configured to retain the key device in the cavity.

5. The injection device as claimed in claim 4, wherein the injection device is configured to retain the key device in the cavity by friction.

6. The injection device as claimed in claim 4, wherein the injection device includes a catch mechanism to retain the key device in the cavity.

7. The injection device as claimed in claim 1, wherein the key device is provided with an identifier that is readable by the sensing arrangement.

8. The injection device as claimed in claim 7, wherein the injection device is configured to respond to the sensing arrangement sensing the presence of the key device in the cavity by triggering operation of the injection device only if the identifier read by the sensing arrangement meets a predetermined criterion.

9. The injection device as claimed in claim 7, configured to limit a dose size and/or a delivery rate of medicament delivered dependent on the identifier read from the sensing arrangement.

10. The injection device as claimed in claim 1, wherein the device is a bolus injector that is configured to be attached to a user for a duration of delivery of medicament.

11. The injection device as claimed in claim 1, further comprising:
   a medicament container coupled to the medicament delivery arrangement.

12. The device of claim 11, wherein the medicament container contains a medicament.

13. The device of claim 12, wherein the medicament comprises a pharmaceutically active compound.

14. A method of operating an injection device comprising a needle insertion mechanism, a medicament delivery arrangement configured to cause injection of a medicament into a patient, a cavity comprising an opening configured to receive a key device such that a possibility of accidental triggering by unintentional pressing of a button or similar is avoided, and a sensing arrangement configured to sense a presence or an absence of the key device in the cavity, the method comprising:
responding to detecting that the key device, which has previously been external to the cavity, has been inserted into the cavity to be present in the cavity by causing powering of the needle insertion mechanism to insert a needle into the patient.

15. An injection device comprising:
a needle insertion mechanism;
a medicament delivery arrangement configured to cause injection of a medicament into a patient; and
a cavity having an opening for receiving a key device, the key device comprising electrical cells and being operable to provide electrical energy to the injection device, wherein the injection device is configured to respond to detecting a presence of the key device in the cavity by triggering operation of the injection device.

16. An injection device as claimed in claim 15, the injection device further comprising a sensing arrangement for sensing the presence or absence of the key device in the cavity, wherein the injection device is configured to respond to the sensing arrangement sensing the presence of the key device in the cavity by triggering operation of the injection device, and wherein the sensing arrangement comprises a detector for detecting the presence of an electrical voltage, the voltage indicating the presence of the key device within the cavity.

17. An injection device as claimed in claim 16, wherein the detector is configured to detect the presence of the electrical voltage across a first electrical terminal and a second electrical terminal.

18. An injection device as claimed in claim 17, wherein at least one of the first electrical terminal and the second electrical terminal has the form of a ring such that the key device can be inserted into the cavity in any rotational direction.

19. An injection device as claimed in claim 17, wherein at least one of the first electrical terminal and the second electrical terminal is recessed.

20. An injection device as claimed in claim 15, wherein the key device is further provided with an identifier that is readable by a sensing arrangement.

21. An injection device as claimed in claim 20, wherein the injection device configured to respond to the sensing arrangement sensing the presence of the key device in the cavity by triggering operation of the injection device only if the identifier read by the sensing arrangement meets a predetermined criterion.

22. An injection device as claimed in claim 15, wherein the injection device is configured to respond to detecting the presence of the key device in the cavity by powering of a needle insertion mechanism to insert a needle into the patient.

23. An injection device as claimed in claim 22, wherein the needle insertion mechanism comprises a needle insertion mechanism driver configured to insert the needle into the patient, and wherein the key device is configured to supply sufficient electrical power to the needle insertion mechanism driver.

24. An injection device as claimed in claim 15, wherein the injection device is configured to respond to detecting the presence of the key device in the cavity by causing commencement of delivery of medicament into the patient.

* * * * *